United States Patent [19]

Szonntagh

[11] 4,315,430
[45] Feb. 16, 1982

[54] GAS CALORIFIC CONTENT ANALYZING APPARATUS

[75] Inventor: Eugene L. Szonntagh, Flourtown, Pa.

[73] Assignee: Honeywell Inc., Minneapolis, Minn.

[21] Appl. No.: 123,411

[22] Filed: Feb. 21, 1980

[51] Int. Cl.³ .......................................... G01N 25/30
[52] U.S. Cl. ............................................... 73/190 CV
[58] Field of Search ....................... 73/190 R, 190 CV

[56] References Cited

U.S. PATENT DOCUMENTS

| | | | |
|---|---|---|---|
| 977,970 | 12/1910 | Sawford | 73/190 CV |
| 2,285,866 | 6/1942 | Markle | 73/190 R |
| 2,603,085 | 7/1952 | Cannon | 73/190 CV |
| 2,666,584 | 1/1954 | Kliever . | |
| 3,033,985 | 5/1962 | Petree . | |
| 3,049,300 | 8/1962 | Lewis et al. . | |
| 3,101,618 | 8/1963 | Hance . | |
| 3,187,559 | 6/1965 | Cox . | |
| 3,393,562 | 7/1968 | Breedlove | 73/190 CV |
| 3,460,385 | 8/1969 | Kolster | 73/190 CV |
| 3,738,810 | 6/1973 | Clinton et al. . | |
| 3,777,562 | 12/1973 | Clingman | 73/190 CV |
| 3,960,320 | 6/1976 | Slater . | |

FOREIGN PATENT DOCUMENTS

| | | | |
|---|---|---|---|
| 116845 | 3/1930 | Austria | 73/190 R |
| 661796 | 3/1929 | France | 73/190 R |

Primary Examiner—James J. Gill
Attorney, Agent, or Firm—Laurence J. Marhoefer; Lockwood D. Burton; Mitchell J. Halista

[57] ABSTRACT

A gas analyzing apparatus for determining the BTU or calorific content of a combustible gas uses a radiometer or optical pyrometer for measuring the temperature of a metal cup black body heated by a flame produced by a combustion of the combustible gas in a gas-air mixture and a valve controller responsive to a control signal for adjusting the air-gas ratio, thermistors for measuring the temperature of the gas-air mixture and the ambient temperature and a temperature monitor including means responsive to the output signals from the radiometer and the thermistors to produce an output signal representative of the temperature difference therebetween and a peak detector responsive to the output signal from the temperature monitor means to produce the control signal for controlling the valve controller to obtain a peak in the output signal from the temperature monitor, whereby to obtain a maximum temperature differential between the metal cup and air-gas mixture with the attained differential temperature being an indication of the BTU content of the combustible gas being measured since the maximum temperature differential would be attained at stoichiometric combustion for any combustible gas being tested.

12 Claims, 1 Drawing Figure

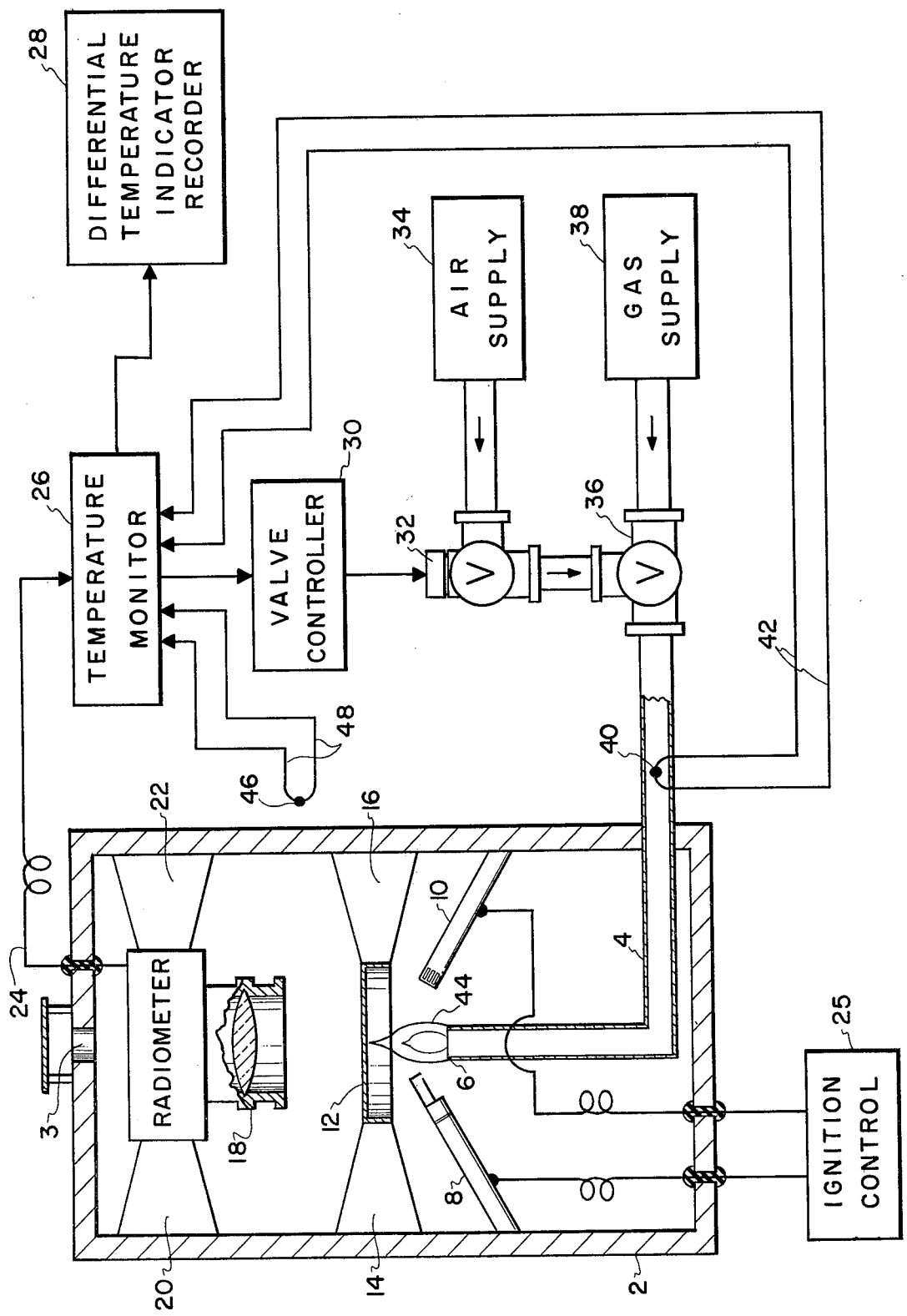

GAS CALORIFIC CONTENT ANALYZING APPARATUS

BACKGROUND OF THE INVENTION

1. Field of the Invention

The present invention relates to gas analyzers. More specifically, the present invention is directed to a gas analyzer for determining the BTU or calorific content of a combustible gas.

2. Description of the Prior Art

The measurement of BTU or caloric content of a combustible gas such as that supplied for home heating, etc., provides a measure of the quality of the gas being supplied and, hence, the appropriate rate or cost for the gas can be billed to a customer who formerly was charged a rate based simply on cubic volume of gas consumption. Conventional gas analyzers for determining the composition of an unknown gas are well-known in the art. The basic analyzer is known as the Orsat type and is used to absorb the constituent gases one at a time from a gas mixture and to determine the constituent quantities from the resulting decreases in the gas pressure. The resulting gas analysis could be used as a basis for customer billing. However, such an apparatus is wholly inpractical for mass installation in gas consumer locations. Another prior art gas analyzer is based on the use of the thermal conductivity of the unknown gas which gas is analyzed by comparing its rate of thermal conductivity with that of a standard reference gas. Another prior art gas analyzing device used, in various arrangements, a catalyzing wire which has its temperature affected by a gas being burned adjacent to the wire to produce an output signal which is used to ascertain the percentage of combustible gas in the gas being tested. Still another group of prior art gas analyzers were based on an optical analysis of the color, etc. of a gas flame to provide a measure of combustible gas content. All of these prior art devices have serious shortcomings in providing a rapid and accurate measure of the BTU content of the combustible gas while utilizing a compact and simple structure suitable for mass production and capable of being mounted in unattended customer locations. Accordingly, it is desirable to provide a BTU meter capable of determining the BTU or caloric content of an unknown gas composition to provide a measure of the billing cost to be assigned to the gas during a sale of the gas to a consumer.

SUMMARY OF THE INVENTION

An object of the present invention is to provide an improved calorimeter for determining the BTU for calorific content of a combustible gas.

In accomplishing this and other objects, there has been provided, in accordance with the present invention, a calorimeter having means for determining the temperature produced by the combustion of a gas to be measured and means responsive to the temperature measuring means for adjusting the air/gas ratio to achieve stoichiometric combustion to produce a maximum temperature. The temperature achieved is a measure of the relative BTU or calorific content of the combustible gas.

BRIEF DESCRIPTION OF THE DRAWING

A better understanding of the present invention may be had when the following detailed description is read in connection with the accompanying drawing, in which the single FIGURE drawing is a block diagram of a calorimeter embodying an example of the present invention.

DETAILED DESCRIPTION OF THE PREFERRED EMBODIMENT

Referring to a single FIGURE drawing in more detail, there is shown a calorimeter having a gas combustion chamber 2 with a restricted exhaust port 3. The gas combustion chamber 2 has a gas pipeline 4 passing through a wall of the chamber and terminating in a gas jet 6. A gas igniting spark is produced by a gas igniter 8 attached to the wall of the chamber 2 and having a spark producing element adjacent to the gas jet 6. A flame sensor 10 is provided adjacent to the gas jet 6 and is arranged to produce an output signal indicative of the presence of a gas flame at the gas jet 6. A metal cup 12, which functions as a so-called "black body", is suspended by thermally isolating fins 14 and 16 from the walls of the chamber 2 adjacent to the gas jet 6. The gas jet 6 is located on one side of the metal cup 12 while a radiometer or optical pyrometer 18 is located on the other side of the metal cup 12. The radiometer 18 is used to measure the temperature of the metal cup produced by the burning of the combustible gas at the gas jet 6. The radiometer 18 is suspended by fins 20 and 22 from the walls of the chamber 2 and has an output signal line 24. An ignition control 25 is arranged to control the ignition of the gas flame by the ignitor 8 and to receive a signal from the gas flame sensor 10 to monitor the presence of the gas flame at the gas jet 6.

The output signal from the radiometer 18 on the output line 24 is applied to a temperature monitor 26. The temperature monitor 26, in turn, produces an output signal indicative as hereinafter discussed of the temperature achieved by combustion of the gas to a differential temperature indicator recorder 28 and an output control signal for controlling a valve controller 30. The temperature monitor 26 includes any suitable prior art device for comparing a present input signal with a preceding input signal to determine whether or not a peak signal level has been reached and to produce an output control signal until the peak is detected, such peak detectors being well-known in the art. The valve controller 30, in turn, is arranged to use the control signal from the temperature monitor 26 to selectively operate a control valve 32. The control valve 32 is arranged to control the volume of air being supplied from an air supply 34 to a mixing valve 36 in combination with the combustible gas being measured supplied from a gas supply 38 having a fixed, or constant, flow rate to produce a gas-air mixture.

In order to compensate the temperature measurement by the radiometer 18 for the BTU's introduced by the gas-air mixture and the ambient temperature, a temperature measuring element, e.g., thermistor 40, is located within the pipeline 4 to measure the temperature of the incoming gas-air mixture and to produce an output signal on line 42 which is applied to the temperature monitor 26. A second thermistor 46 is located adjacent to the outside of the thermally insulated housing 2 to measure the ambient temperature. The output signal from the second thermistor 46 is applied on line 48 to the monitor 26. Thus, the output signal from the temperature monitor 26 to the indicator 28 is representative of the difference between the temperature of the metal cup 12 and the combined effect of the temperature of the incoming mixture in the pipeline 4 and the ambient temperature with the peak detector monitoring this differential temperature output signal to detect a peak thereof. The temperature indicator 28 may include a recorder or other devices to provide a visual indication and/or a record of the differential temperature which is a measure of the BTU or calorific content of a gas being burned at the gas jet 6.

In operation, the flame is initially ignited at the gas jet 6 by the ignition control 25 to produce a gas flame 44. The gas flame 44 is effective to heat the cup 12 to a temperature as determined by the air/fuel ratio being supplied to the gas flame 44 the heat losses in the apparatus and the caloric input from the air/fuel mixture temperature and the ambient temperature. The use of the cup 12 avoids inaccuracies which could arise in the direct measurement of the temperature of the flame 44 by providing a uniform temperature surface. The restricted port 3 allows the escape of the burned gases while preventing the entrance of excess air which could affect the air/fuel ratio at the flame 44. The temperature of the cup 12 is sensed by the radiometer 18 to produce an input signal to the temperature monitor 26 along with an input signal from the thermistors 40 and 44. The temperature monitor 26 is, in turn, produces a control signal to a valve controller 30 based on the difference in temperature between the radiometer measurement and the temperature measurement by the thermistors 40 and 44 to produce a change in the air/fuel mixture by means of control valve 32 and a differential temperature output signal to the indicator 28. If the differential temperature output signal being monitored by the peak detector in the monitor 26 following such a change in the air/fuel ratio is indicative of an increase in the differential temperature of the cup 12 and the incoming mixture and the ambient temperature, the air/fuel ratio is changed again in the same direction by the valve controller 30 and temperature monitor 26. This air/fuel change is continued until a decrease in the differential temperature of the cup 12 and the incoming mixture and ambient temperature is sensed by the peak detector in the monitor 26 which is indicative of the attainment of stoichiometric combustion at the preceding air/fuel ratio value. The differential temperature at that preceding air/fuel ratio value as indicated by the output signal supplied by the monitor 26 to the indicator 28 is the measure of the BTU content of the particular combustible gas being burned at the gas jet 6. By comparing a differential temperature indication for one gas sample with an indication for another gas sample, a relative BTU or calorific content can be ascertained to support a corresponding customer billing.

In order to simplify the aforesaid structure of the illustrated example of an embodiment of the present invention, additional elements which can be added to the basic structure have been omitted. For example, the ignition control can include timer means for periodically lighting the flame at the gas jet 6 and a control valve could be inserted in the pipeline 4 to respond to the timer means by periodically turning off the gas mixture flow between ignition cycles. Further, the radiometer 18 could be replaced by any suitable temperature measuring device capable of providing the desired accuracy of temperature measurement. Additionally, the indicator 28 can include an analog to digital converter, a digital display and a digital receiver/transmitter whereby a remote operation of the entire apparatus could be effected with an installation of the analyzer directly at a customer site. Such a remote control arrangement would, of course, require additional selective control of the ignition control 25 and any timer associated therewith. Finally, the ambient temperature thermistor 46 can be eliminated by providing a heat exchanger for the air/fuel mixture to allow it to attain the ambient temperature whereby a measurement of the temperature of only the air/fuel mixture would be sufficient to determine the attained differential temperature.

Accordingly, it may be seen that there has been provided, in accordance with the present invention, a gas analyzer for determining the relative BTU or calorific content of combustible gases.

The embodiments of the invention in which an exclusive property or privilege is claimed are defined as follows:

1. A gas calorific analyzer comprising
   gas-air ratio control means for controlling a gas-air mixture,
   combustion means for producing combustion of said gas-air mixture,
   means for producing an output signal representative of the temperature increase produced by the combustion of the gas-air mixture,
   peak detecting means responsive to said output signal to control said control means to change the gas-air ratio until a peak is detected in said output signal and
   indicating means for producing an indication of said output signal as a measure of the calorific content of the gas to be analyzed wherein said means for producing an output signal includes a "black body" heated by the combustion of said gas-air mixture and a temperature detecting means for monitoring the temperature difference between said "black body", said gas-air mixture and an ambient temperature of the environment of said gas analyzer.

2. A gas analyzer as set forth in claim 1 wherein said ratio control means includes a selectively controllable gas flow valve.

3. A gas analyzer as set forth in claim 1 wherein said means for producing an output signal includes a thermistor located in a gas-air pipeline supplying said gas-air mixture before combustion by said combustion means and an ambient temperature measuring thermistor.

4. A gas analyzer as set forth in claim 1 wherein said combustion means includes a gas jet, means for igniting said gas-air mixture at said gas jet, means for sensing the presence of a flame at said gas jet and an ignition control means responsive to said means for sensing to operate said means for igniting.

5. A gas analyzer as set forth in claim 4 wherein said combustion means includes a sealed combustion chamber enclosing at least said gas jet and said means for igniting, and having an exhaust gas port and an inlet pipeline passing through a wall of said chamber to connect said gas jet to a source of said gas-air mixture.

6. A gas analyzer as set forth in claim 5 wherein said means for producing said output signal includes a "black body" within said combustion chamber and arranged to be heated by the combustion of said gas-air mixture and a temperature detecting means for monitoring the temperature difference between said "black body" and said gas-air mixture and an ambient temperature of the environment of said gas analyzer.

7. A gas analyzer comprising
   gas-air ratio control means for controlling a gas-air mixture, combustion means for producing combustion of said gas-air mixture, means for producing an output signal representative of the temperature increase produced by the combustion of the gas-air mixture, peak detecting means responsive to said output signal to control said control means to change the gas-air ratio until a peak is detected in said output signal and indicating means for producing an indication of said output signal as a measure of the gas to be analyzed, said means for producing an output signal including a "black body" heated by the combustion of said gas-air mixture and a temperature detecting means for monitoring the temperature difference between said "black body", said gas-air mixture and an ambient temperature of the environment of said gas analyzer.

8. A gas analyzer as set forth in claim 7 wherein said means for producing an output signal includes a thermistor located in a gas-air pipeline supplying said gas-air mixture before combustion by said combustion means and an ambient temperature measuring thermistor.

9. A gas analyzer as set forth in claim 7 wherein said combustion means includes a gas jet, means for igniting said gas-air mixture at said gas jet, means for sensing the presence of a flame at said gas jet and an ignition control means responsive to said means for sensing to operate said means for igniting.

10. A gas analyzer as set forth in claim 9 wherein said combustion means includes a sealed combustion chamber enclosing at least said gas jet and said means for igniting, and having an exhaust gas port and an inlet pipeline passing through a wall of said chamber to connect said gas jet to a source of said gas-air mixture.

11. A gas analyzer as set forth in claim 10 wherein said means for producing said output signal includes a "black body" within said combustion chamber and arranged to be heated by the combustion of said gas-air mixture and a temperature detecting means for monitoring the temperature difference between said "black body" and said gas-air mixture and an ambient temperature of the environment of said gas analyzer.

12. A gas analyzer as set forth in claim 7 wherein said ratio control means includes a selectively controllable gas flow valve.

* * * * *